United States Patent [19]

Hutchison et al.

[11] Patent Number: 4,746,653
[45] Date of Patent: May 24, 1988

[54] CERTAIN HETERO PHOSPHONIC ACID DERIVATIVES OF 2-PIPERIDINE OR 2-TETRAHYDROPYRIDINECARBOXY-LATES AND ESTERS THEREOF WHICH ARE USEFUL FOR THE TREATMENT OF DISORDERS RESPONSIVE TO BLOCKADE OF THE NMDA RECEPTOR IN MAMMALS

[75] Inventors: Alan J. Hutchison, Vernona; Kenneth R. Shaw; Josef A. Schneider, both of Millburn, all of N.J.

[73] Assignee: Ciba-Geigy Corporation, Ardsley, N.Y.

[21] Appl. No.: 834,672

[22] Filed: Feb. 28, 1986

[51] Int. Cl.$^4$ .................. C07F 9/58; C07F 9/65; A61K 31/675
[52] U.S. Cl. .................. 514/89; 546/22; 546/23; 546/24; 548/413
[58] Field of Search .................. 546/22, 24; 514/89

[56] References Cited

U.S. PATENT DOCUMENTS 4,477,391  10/1984  Collins .................. 260/502.56
4,483,853  11/1984  Collins .................. 514/141

FOREIGN PATENT DOCUMENTS 0117429  8/1984  European Pat. Off. .......... 558/170
3510858A  8/1984  Fed. Rep. of Germany ...... 558/169
2157685  10/1985  United Kingdom .......... 544/337

OTHER PUBLICATIONS

Simon, R. P. et al., Science, 226, 850–852, (1984).
Neuroscience Abstracts, 11, 106, (1985).
Epilepsia, 25, (Supple. 2), S140–S149, (1984).
Neuropharmacology, 23, 467–472, (1984).
Tetrahedron Letters, 1979, 4929–4930, (1979).
Medicinal Research Reviews, 2, 1–41, (1982).
Chem. Pharmaceutical Bulletin, 32, 3918–3925, (1984).

*Primary Examiner*—Alan L. Rotman
*Attorney, Agent, or Firm*—Norbert Gruenfeld

[57] ABSTRACT

The present invention is concerned with the phosphonic acids of formula I

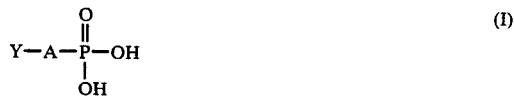

wherein one or both of the acidic hydroxy groups of the phosphonic acid moiety may be functionalized in form of pharmaceutically acceptable mono- or di-esters; wherein Y represents optionally substituted 2-carboxypyrrolidinyl, 2-carboxy-2,5-dihydropyrrolyl, 2-carboxy-1,2,3,6-tetrahydropyridinyl, 2-carboxy-1,2,5,6-tetrahydropyridinyl, 2-carboxypiperidinyl, 2-carboxytetrahydroquinolinyl or 2-carboxyperhydroquinolinyl, 2-carboxy-2,3-dihydroindolyl, 2-carboxyperhydroindolyl, and in each of which the carboxy group may be functionalized in form of a pharmaceutically acceptable ester or amide; A represents B—X—D wherein B represents a direct bond, or straight chain or branched lower alkylene; X represents O, S, SO, SO$_2$, CO—NR$_b$, R$_b$N—CO or N—Ra; Ra represents hydrogen, lower alkyl, aryl, aryl-lower alkyl or acyl; R$_b$ represents hydrogen, lower alkyl or aryl-lower alkyl; D represents straight chain or branched lower alkylene; and pharmaceutically acceptable salts thereof; which are useful in mammals as antagonists of the N-methyl-D-aspartate sensitive excitatory amino acid receptor.

16 Claims, No Drawings

CERTAIN HETERO PHOSPHONIC ACID DERIVATIVES OF 2-PIPERIDINE OR 2-TETRAHYDROPYRIDINECARBOXYLATES AND ESTERS THEREOF WHICH ARE USEFUL FOR THE TREATMENT OF DISORDERS RESPONSIVE TO BLOCKADE OF THE NMDA RECEPTOR IN MAMMALS

SUMMARY OF THE INVENTION

The present invention is concerned with the phosphonic acids of formula I

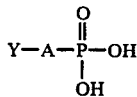
(I)

wherein one or both of the acidic hydroxy groups of the phosphonic acid moiety may be functionalized in form of pharmaceutically acceptable mono- or di-esters; wherein Y represents optionally substituted 2-carboxypyrrolidinyl, 2-carboxy-2,5-dihydropyrrolyl, 2-carboxy-1,2,3,6-tetrahydropyridinyl, 2-carboxy-1,2,5,6-tetrahydropyridinyl, 2-carboxypiperidinyl, 2-carboxytetrahydroquinolinyl or 2-carboxyperhydroquinolinyl, 2-carboxy-2,3-dihydroindolyl, 2-carboxyperhydroindolyl, and in each of which the carboxy group may be functionalized in form of a pharmaceutically acceptable ester or amide; A represents B-X-D wherein B represents a direct bond, or straight chain or branched lower alkylene; X represents O, S, SO, SO$_2$, CO-NR$_b$, R$_b$N-CO or N-Ra; Ra represents hydrogen, lower alkyl, aryl, aryl-lower alkyl or acyl; R$_b$ represents hydrogen, lower alkyl or aryl-lower alkyl; D represents straight chain or branched lower alkylene; and pharmaceutically acceptable salts thereof; which are useful in mammals as antagonists of the N-methyl-D-aspartate sensitive excitatory amino acid receptor.

The instant invention is further concerned with processes for preparing said compounds, with pharmaceutical compositions comprising said compounds, with a method of blocking the N-methyl-D-aspartate excitatory amino acid receptor, and with a method of treating conditions and diseases in mammals responsive to the effect of an excitatory amino acid receptor antagonist by administration of said compounds or of pharmaceutical compositions comprising said compounds.

The compounds of the invention are active and useful as selective antagonists of the N-methyl-D-aspartate (NMDA) excitatory amino acid receptor. The compounds of the invention are therefore also useful, administered alone or in combination to mammals, for the treatment of disorders responsive to said blockade of the NMDA receptor, comprising e.g. cerebral ischaemia, muscular spasms (spasticity), convulsive disorders (epilepsy) and anxiety.

DETAILED DESCRIPTION OF THE INVENTION

One aspect of the invention relates to the phosphonic acid derivatives of formula I and derivatives thereof wherein Y represents optionally substituted 2-carboxypiperidinyl, 2-carboxy-1,2,3,6-tetrahydropyridinyl or 2-carboxy-1,2,5,6-tetrahydropyridinyl, more specifically the compounds of the formula II

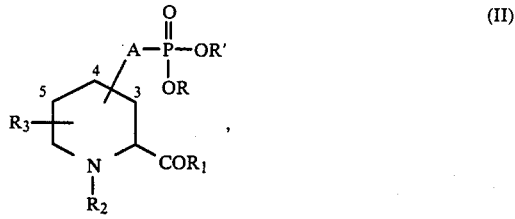

and the compounds of formula II with a double bond present between the 3 and 4 or between 4 and 5 carbon atoms of the piperidyl ring, in which the phosphono bearing chain is attached at the 3, 4, or 5-position of the piperidinyl or tetrahydropyridinyl ring, and wherein R and R' represent hydrogen, lower alkyl, benzyl, benzyl substituted on phenyl by halogen, lower alkyl or lower alkoxy, lower alkanoyloxymethyl, lower alkanoyloxymethyl substituted on oxymethyl by lower alkyl, cyclohexyl or cyclopentyl; R$_2$ represents hydrogen, lower alkyl, aryl-lower alkyl, lower alkanoyl or aroyl; R$_3$ represents hydrogen, lower alkyl or aryl-lower alkyl; COR$_1$ represents carboxy or carboxy derivatized in the form of a pharmaceutically acceptable ester or amide; A represents

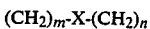 (A)

(CH$_2$)$_m$ being attached to the ring, wherein m represents zero, 1, 2 or 3; n represents 1, 2 or 3; X represents O, S, SO, SO$_2$, CO-NR$_b$, R$_b$N-CO or N-Ra; Ra represents hydrogen, lower alkyl, aryl, aryl-lower alkyl or acyl; R$_b$ represents hydrogen, lower alkyl or aryl-lower alkyl; and wherein one or more of carbon atoms within A may be substituted by lower alkyl, aryl or aryl-lower alkyl; and pharmaceutically acceptable salts thereof.

Preferred are the said compounds, and more particularly those of formula II, wherein R and R' independently represent hydrogen, benzyl, lower alkyl, lower alkanoyloxymethyl or lower alkanoyloxymethyl substituted on oxymethyl by lower alkyl, cyclohexyl or cyclopentyl; A represents (CH$_2$)$_m$-X-(CH$_2$)$_n$; m represents zero, 1 or 2; n represents 1 or 2; X represents O, S, SO, SO$_2$, CO-NR$_b$, R$_b$N-CO or NRa; Ra represents hydrogen, lower alkyl, benzyl, lower alkanoyl or aroyl; R$_b$ represents hydrogen, lower alkyl or benzyl; COR$_1$ represents carboxy, carbamoyl or carboxy esterified in form of a pharmaceutically acceptable ester; R$_2$ and R$_3$ represent hydrogen or lower alkyl; and pharmaceutically acceptable salts thereof.

Further preferred are the above compounds of formula II wherein R and R' represent hydrogen, lower alkanoyloxymethyl or lower alkanoyloxymethyl substituted on oxymethyl by lower alkyl; A is located at the 4-position; R$_2$ and R$_3$ represent hydrogen; COR$_1$ represents carboxy, carbamoyl or carboxy esterified in form of a pharmaceutically acceptable ester; and pharmaceutically acceptable salts thereof.

Particularly preferred are the compounds of formula III

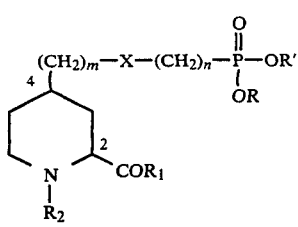

(III)

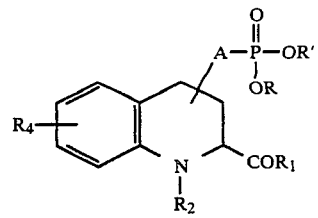

(IV)

wherein m represents zero or the integer 1 or 2; n represents the integer 1 or 2; X represents O, S, SO$_2$, CO-NR$_b$, R$_b$N-CO or N-Ra in which Ra represents hydrogen, lower alkyl, lower alkanoyl, benzoyl, nicotinoyl, N-lower alkyl-1,4-dihydronicotinoyl, or benzoyl substituted by lower alkyl, by lower alkoxy, by halogen or by trifluoromethyl, and R$_b$ represents hydrogen or lower alkyl; R and R' independently represent hydrogen, lower alkyl, benzyl, lower alkanoyloxymethyl or lower alkanoyloxymethyl substituted on oxymethyl by lower alkyl; COR$_1$ represents carboxy, carboxy esterified in the form of a pharmaceutically acceptable ester, or carbamoyl; R$_2$ represents hydrogen, lower alkyl, lower alkanoyl, nicotinoyl, N-lower alkyl-1,4-dihydronicotinoyl, benzoyl or benzoyl substituted by lower alkyl, by lower alkoxy, by halogen or by trifluoromethyl; and pharmaceutically acceptable salts of said compounds having a salt-forming functional grouping.

Particular embodiments relate to the compounds of formula II and III wherein X represents either O, S, SO, SO$_2$, CO-NR$_b$, R$_b$N-CO or N-Ra as defined herein.

Most preferred are the compounds of formula III wherein the 2- and 4-substituents are cis to each other.

Further preferred are the said compounds of formula III wherein m represents zero or the integer 1 or 2; X represents O, S, CO-NR$_b$, R$_b$N-CO or N-Ra as defined above; n represents the integer 1 or 2; R and R' both represent hydrogen, lower alkyl or lower alkanoyloxymethyl; or one of R and R' represents hydrogen and the other of R and R' represents lower alkyl, benzyl, lower alkanoyloxymethyl or lower alkanoyloxymethyl substituted on oxymethyl by lower alkyl; R$_2$ represents hydrogen; COR$_1$ represents carboxy or carboxy esterified in form of a pharmaceutically acceptable ester; and pharmaceutically acceptable salts thereof.

A preferred embodiment relates to the compounds, preferably cis, of formula III wherein m represents zero or 1; X represents NH-CO, N-(lower alkyl)-CO, NH or N-lower alkyl; n represents the integer 1 or 2; R and R' represent hydrogen; COR$_1$ represents carboxy or carboxy esterified in form of a pharmaceutically acceptable ester; R$_2$ represents hydrogen; and pharmaceutically acceptable salts thereof.

Another aspect of the invention relates to the phosphonic acid derivatives of formula I and derivatives cited above wherein Y represents 2-carboxy-1,2,3,4-tetrahydro- or perhydroquinolinyl in which the phosphono bearing chain is preferably located at the 3 or 4 position of the tetrahydro or perhydroquinolinyl ring, i.e. the compounds of formula IV or perhydro derivatives thereof, wherein A represents $$(CH_2)_m\text{-}X\text{-}(CH_2)_n \quad (A)$$

(CH$_2$)$_m$ being attached to the ring, wherein m represents zero, 1, 2 or 3; n represents 1, 2 or 3; X represents O, S, SO, SO$_2$, CO-NR$_b$, R$_b$N-CO or N-Ra; Ra represents hydrogen, lower alkyl, aryl, aryl-lower alkyl or acyl; R$_b$ represents hydrogen, lower alkyl or aryl-lower alkyl; and wherein one or more of carbon atoms within A may be substituted by lower alkyl, aryl or aryl-lower alkyl; R and R' represent hydrogen, lower alkyl, benzyl, benzyl substituted on phenyl by halogen, lower alkyl or lower alkoxy; or R and R' represent lower alkanoyloxymethyl, lower alkanoyloxymethyl substituted on oxymethyl by lower alkyl, cyclohexyl or cyclopentyl; COR$_1$ represents carboxy or carboxy functionalized in the form of a pharmaceutically acceptable ester or amide; R$_2$ represents hydrogen, lower alkyl, aryl-lower alkyl, lower alkanoyl or aroyl; R$_4$ represents hydrogen, lower alkyl, lower alkoxy, halogen or trifluoromethyl; and pharmaceutically acceptable salts thereof.

Preferred are the compounds of formula V

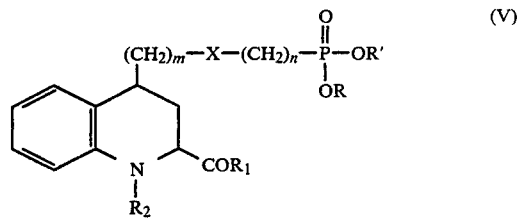

(V)

or the perhydroquinoline derivatives thereof wherein m represents zero or the integer 1 or 2; n represents the integer 1 or 2; X represents O, S, SO$_2$, CO-NR$_b$, RN-CO or N-Ra; Ra represents hydrogen, lower alkyl, lower alkanoyl, benzoyl, nicotinoyl, N-lower alkyl-1,4-dihydronicotinoyl, or benzoyl substituted by lower alkyl, by lower alkoxy, by halogen or by trifluoromethyl; R$_b$ represents hydrogen or lower alkyl; R and R' independently represent hydrogen, lower alkyl, benzyl, lower alkanoyloxymethyl or lower alkanoyloxymethyl substituted on oxymethyl by lower alkyl; COR$_1$ represents carboxy, carboxy esterified in the form of a pharmaceutically acceptable ester, or carbamoyl; R$_2$ represents hydrogen, lower alkyl, lower alkanoyl, nicotinoyl, N-lower alkyl-1,4-dihydronicotinoyl, benzoyl or benzoyl substituted by lower alkyl, by lower alkoxy, by halogen or by trifluoromethyl; and pharmaceutically acceptable salts of said compounds having a salt-forming functional grouping.

Most preferred are the compounds of formula V and perhydroquinoline derivatives hereof wherein the 2- and 4-substituents are cis to each other.

Further preferred are said compounds of formula V and perhydroquinoline derivatives thereof wherein m represents zero, 1 or 2; n represents the integer 1 or 2; R and R' both represent hydrogen or lower alkanoyloxymethyl; or one of R and R' represents hydrogen and the other of R and R' represents lower alkyl, benzyl, lower alkanoyloxymethyl, or lower alkanoyloxymethyl substituted on oxymethyl by lower alkyl; $R_2$ represents hydrogen; $COR_1$ represents carboxy or carboxy esterified in form of a pharmaceutically acceptable ester; and pharmaceutically acceptable salts thereof.

A preferred embodiment relates to the compounds, preferably cis, of formula V and the perhydroquinoline derivatives thereof, wherein m represents zero or 1; n represents the integer 1 or 2; X represents O, S, NH-CO, N-(lower alkyl)-CO, NH or N-lower alkyl; R and R' represent hydrogen; $COR_1$ represents carboxy or carboxy esterified in form of a pharmaceutically acceptable ester; $R_2$ represents hydrogen; and pharmaceutically acceptable salts thereof.

A further aspect of the invention relates to the phosphonic acid derivatives of formula I and derivatives cited above wherein Y represents optionally sbstituted 2-carboxypyrrolidinyl, i.e. the compounds of formula VI

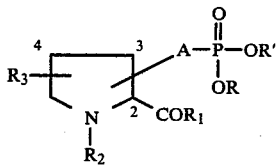

and the compounds of formula VI with a double bond present between the 3 and 4 carbon atoms of the pyrrolidinyl ring, in which the phosphono bearing chain is attached preferably at the 3 or 4 position of the pyrrolidine ring and wherein R and R' represent hydrogen, lower alkyl, benzyl, benzyl substituted on phenyl by halogen, lower alkyl, or lower alkoxy; or R and R' represent lower alkanoyloxymethyl, lower alkanoyloxymethyl substituted on oxymethyl by lower alkyl, cyclohexyl or cyclopentyl; $R_2$ represents hydrogen, lower alkyl, lower alkanoyl or aroyl; $R_3$ represents hydrogen, lower alkyl or aryl-lower alkyl; $COR_1$ represents carboxy or carboxy derivatized in the form of pharmaceutically acceptable ester or amide; A represents $(CH_2)_m\text{-X-}(CH_2)_n$ (A)

$(CH_2)_m$ being attached to the ring, wherein m represents zero, 1, 2 or 3; n represents 1, 2 or 3; X represents O, S, SO, SO$_2$, CO-NR$_b$, R$_b$N-CO or N-Ra; Ra represents hydrogen, lower alkyl, aryl, aryl-lower alkyl or acyl; R$_b$ represents hydrogen, lower alkyl or aryl-lower alkyl; and wherein one or more of carbon atoms within A may be substituted by lower alkyl, aryl or aryl-lower alkyl; and pharmaceutically acceptable salts thereof.

Preferred are the compounds of formula VI wherein the phosphono bearing group is attached at the 3 or 4-position, advantageously at the 4-position; $R_2$ and $R_3$ represent hydrogen; R and R' represent hydrogen or lower alkanoyloxymethyl; $COR_1$ represents carboxy, carbamoyl or carboxy esterified in form of a pharmaceutically acceptable ester; m represents 0 or 1; n represents 1 or 2; and X represents O, S, NH-CO, N-(lower alkyl)-CO, NH or N-lower alkyl; $R_2$ represents hydrogen; and pharmaceutically acceptable salts.

Another aspect of the invention relates to the phosphonic acid derivatives of formula I and derivatives cited above wherein Y represents 2-carboxy-2,3-dihydro- or perhydroindolyl in which the phosphono bearing chain is preferably located at the 3 position of the dihydro or perhydroindolyl ring, i.e. the compounds of formula VII

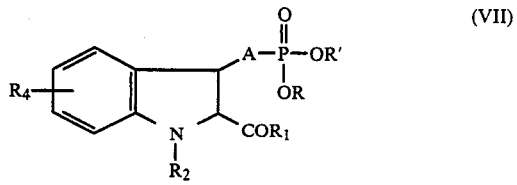

or perhydro derivatives thereof, wherein A represents $(CH_2)_m\text{-X-}(CH_2)_n$ (A)

$(CH_2)_m$ being attached to the ring wherein m represents zero, 1, 2 or 3; n represents 1, 2 or 3; X represents O, S, SO, SO$_2$, CO-NR$_b$, R$_b$N-CO or N-Ra; Ra represents hydrogen, lower alkyl, aryl, aryl-lower alkyl or acyl; R$_b$ represents hydrogen, lower alkyl or aryl-lower alkyl; and wherein one or more of carbon atoms within A may be substituted by lower alkyl, aryl or aryl-lower alkyl; R and R' represent hydrogen, lower alkyl, benzyl, benzyl substituted on phenyl by halogen, lower alkyl or lower alkoxy; or R and R' represent lower alkanoyloxymethyl, lower alkanoyloxymethyl substituted on oxymethyl by lower alkyl, cyclohexyl or cyclopentyl; $COR_1$ represents carboxy or carboxy functionalized in the form of a pharmaceutically acceptable ester or amide; $R_2$ represents hydrogen, lower alkyl, aryl-lower alkyl, lower alkanoyl or aroyl; $R_4$ represents hydrogen, lower alkyl, lower alkoxy, halogen or trifluoromethyl; and pharmaceutically acceptable salts thereof.

Preferred are the compounds of formula VII or the perhydroindole derivatives thereof wherein m represents zero or the integer 1 or 2; n represents the integer 1 or 2; X represents O, S, SO$_2$, CO-NR$_b$, R$_b$N-CO or N-Ra; Ra represents hydrogen, lower alkyl, lower alkanoyl, benzoyl, nicotinoyl, N-lower alkyl-1,4-dihydronicotinoyl, or benzoyl substituted by lower alkyl, by lower alkoxy, by halogen or by trifluoromethyl; R$_b$ represents hydrogen or lower alkyl; R and R' independently represent hydrogen, lower alkyl, benzyl, lower alkanoyloxymethyl or lower alkanoyloxymethyl substituted on oxymethyl by lower alkyl; $COR_1$ represents carboxy, carboxy esterified in the form of a pharmaceutically acceptable ester, or carbamoyl; $R_2$ represents hydrogen, lower alkyl, lower alkanoyl, or aroyl; $R_4$ represents hydrogen; and pharmaceutically acceptable salts thereof.

A further preferred embodiment relates to the compounds, preferably trans, of formula VII and the perhydroindole derivatives thereof wherein m represents zero or 1; n represents the integer 1 or 2; X represents O, S, NHCO, N-(lower alkyl)-CO, NH or N-lower alkyl; R and R' represents hydrogen; $COR_1$ represents carboxy or carboxy esterified in form of a pharmaceutically acceptable ester; $R_2$ and $R_4$ represent hydrogen; and pharmaceutically acceptable salts thereof.

The general definitions used herein have the following meaning in the context of the invention.

The term "lower", when referred to above and hereinafter in connection with organic groups, radicals or compounds respectively, defines such with up to and including 7, preferably up to and including 4 and advantageously one, two or three carbon atoms.

A lower alkyl group preferably contains 1–4 carbon atoms and represents for example ethyl, propyl, butyl or advantageously methyl.

A lower alkylene group preferably contains 1–4 carbon atoms and represents for example methylene, ethylene, propylene, i.e. 1,2- or 1,3-propylene, butylene, i.e. 1,2-, 1,3- or 1,4-butylene.

A lower alkoxy group preferably contains 1–4 carbon atoms and represents for example, ethoxy, propoxy or advantageously methoxy.

Lower alkanoyl preferably contains 2–7 carbon atoms and represents advantageously acetyl, propionyl, n-butyryl, isobutyryl or pivaloyl.

Lower alkanoyloxy represents advantageously acetoxy, propionyloxy, n- or i-butyryloxy or pivaloyloxy (trimethylacetyloxy).

Halogen is preferably fluorine and chlorine, but may also represent bromine or iodine.

Acyl represents lower alkanoyl, lower alkoxycarbonyl, cycloalkylcarbonyl, cycloalkyloxycarbonyl, cycloalkyl-lower alkoxycarbonyl; also aryl-lower alkanoyl, aryl-lower alkoxycarbonyl, in which aryl preferably represents phenyl or phenyl substituted by preferably lower alkyl, lower alkoxy or halogen; also aroyl which preferably represents benzoyl, or benzoyl substituted preferably by lower alkyl, lower alkoxy or halogen, or nicotinoyl; also N-lower alkyl-1,4-dihydronicotinoyl.

Aryl represents preferably optionally substituted phenyl, e.g. phenyl or phenyl substituted by one to three substituents selected from lower alkyl, lower alkoxy, trifluoromethyl and halogen; or pyridyl, particularly 3-pyridyl.

Aryl-lower alkyl represents preferably aryl-$C_1$–$C_4$-alkyl, aryl having meaning as defined above, advantageously benzyl or 2-phenylethyl.

A lower alkoxycarbonyl group preferably contains 1–4 carbon atoms in the alkoxy portion and represents for example: methoxycarbonyl, propoxycarbonyl, isopropoxycarbonyl or advantageously ethoxycarbonyl.

An N-mono(lower alkyl)-carbamoyl group preferably contains 1–4 carbon atoms in the alkyl portion and is for example N-methylcarbamoyl, N-propylcarbamoyl, or advantageously N-ethylcarbamoyl.

An N,N-di(lower alkyl)-carbamoyl group preferably contains 1–4 carbon atoms in each lower alkyl portion and represents for example N,N-dimethylcarbamoyl, N-methyl-N-ethylcarbamoyl and advantageously N,N-diethylcarbamoyl.

A di-lower alkylamino-N-lower alkylcarbamoyl group preferably represents di-$C_1$–$C_4$-alkylamino-N-$C_2$–$C_4$-alkylcarbamoyl, the two nitrogen atoms being separated by 2–4 carbon atoms and represents for example N-(2-diethylaminoethyl)carbamoyl, N-(3-diethylaminopropyl)carbamoyl.

A mono-lower alkylamino group preferably contains 1–4 carbon atoms and represents for example methylamino, ethylamino, n or i-(propylamino or butylamino).

A di-lower alkylamino group preferably contains 1–4 carbon atoms in each lower alkyl group and represents for example dimethylamino, diethylamino, di-(n-propyl)-amino and di-(n-butyl)-amino.

A di-lower alkylamino-lower alkoxycarbonyl group contains preferably 2–4 carbon atoms in the alkoxy portion, the oxygen and nitrogen atoms being separated by 2–4 carbon atoms, and for example represents N,N-diethylaminoethoxycarbonyl or N,N-diethylaminopropoxycarbonyl.

A pharmaceutically acceptable ester within the context of the present invention represents an ester of a compound of the invention having a carboxy group, preferably a carboxylic acid prodrug ester that may be convertible under physiological conditions to the corresponding free carboxylic acid.

Carboxy esterified in form of a pharmaceutically acceptable ester, preferably represents e.g. lower alkoxycarbonyl; (amino, mono- or di-lower alkylamino)-substituted straight chain $C_2$–$C_5$-lower alkoxycarbonyl; carboxy substituted lower alkoxycarbonyl, e.g. α-carboxy-substituted lower alkoxycarbonyl; lower alkoxycarbonyl-substituted lower alkoxycarbonyl, e.g. α-lower alkoxycarbonyl-substituted lower alkoxycarbonyl; aryl-substituted lower alkoxycarbonyl, e.g. unsubstituted or substituted benzyloxycarbonyl or pyridylmethoxycarbonyl; lower alkanoyloxy-substituted methoxycarbonyl, e.g. pivaloyloxymethoxycarbonyl; (lower alkanoyloxy or lower alkoxy)-substituted lower alkoxymethoxycarbonyl; bicyclo[2,2,1]heptyloxycarbonyl-substituted methoxycarbonyl such as bornyloxycarbonylmethoxycarbonyl; 3-phthalidoxycarbonyl; (lower alkyl, lower alkoxy, halo)substituted 3-phthalidoxycarbonyl; lower alkoxycarbonyloxy-lower alkoxycarbonyl, e.g. 1-(methoxy- or ethoxycarbonyloxy)-ethoxycarbonyl.

Most preferred as carboxylic acid prodrug esters are e.g. the straight chain $C_1$–$C_4$-alkyl ester such as ethyl; the lower alkanoyloxymethyl esters such as pivaloyloxymethyl; the di- lower alkylamino-straight chain $C_2$–$C_4$-alkyl ester such as 2-diethylaminoethyl; the pyridylmethyl esters such as 3-pyridylmethyl.

A pharmaceutically acceptable amide within the context of the present invention represents an amide of a compound of the invention having a carboxy group, preferably a carboxylic acid amide that may be convertible under physiological conditions to the corresponding free carboxylic acid.

Preferred amides are compounds of the invention wherein carboxy is derivatized as carbamoyl, N-mono-lower alkylcarbamoyl such as N-ethylcarbamoyl, N,N-di-lower alkylcarbamoyl such as N,N-diethylcarbamoyl, or di-lower alkylamino-N-lower alkylcarbamoyl such as N-(2-diethylaminoethyl)carbamoyl or N-(3-diethylaminopropyl)carbamoyl, or N-aryl-lower alkylcarbamoyl such as N-benzylcarbamoyl.

Pharmaceutically acceptable salts are preferably metal or ammonium salts or said compounds of the invention having a free phosphonic or carboxy group, more particularly alkali or alkaline earth metal salts, e.g. the sodium, potassium, magnesium or calcium salt; or advantageously crystallizing ammonium salts derived from ammonia or organic amines, such as methylamine, diethylamine, triethylamine, dicylohexylamine, triethanolamine, ethylenediamine, tris-(hydroxymethyl)aminomethane or benzyltrimethylammonium hydroxide. The compounds of the invention which are basic amines form acid addition salts of preferably pharmaceutically acceptable inorganic or organic acids, such as of strong mineral acids, for example hydrohalic, e.g. hydrochloric or hydrobromic acid; sulfuric, phosphoric or nitric acid; aliphatic or aromatic carboxylic or sulfonic acids, e.g. acetic, propionic, succinic, glycolic, lactic, malic, tartaric, gluconic, citric, ascorbic, maleic, fumaric, pyruvic, pamoic, nicotinic, methanesulfonic, ethanesulfonic, hydroxyethanesulfonic, benzenesulfonic, p-toluenesulfonic or naphthalenesulfonic acid.

The compounds of the invention exhibit valuable pharmacological properties, e.g. selectively blocking the N-methyl-D-aspartate excitatory aminoacid receptors in mammals. The compounds are thus useful for treating diseases responsive to excitatory amino acid blockade in mammals, comprising e.g. nervous system disorders, particularly convulsive disorders (epilepsy) and anxiety, as well as cerebral ischaemia.

These effects are demonstrable in in vitro tests or in vivo animal tests using advantageously mammals or tissues or enzyme preparations thereof, e.g. mice, rats, or monkeys. Said compounds can be administered to them enterally or parenterally, advantageously orally or transdermally, or subcutaneously, intravenously or intraperitoneally, for example, within gelatin capsules, or in the form of aqueous suspensions or solutions, respectively. The applied in vivo dosage may range between about 0.01 to 100 mg/kg, preferably between about 0.05 and 50 mg/kg, advantageously between about 0.1 and 10 mg/kg. Said compounds can be applied in vitro in the form of e.g. aqueous solutions and the dosage may range between about $10^{-4}$ molar and $10^{-8}$ molar concentrations.

The inhibitory effect on the NMDA-type excitatory amino acid receptors is determined in vitro by measuring the inhibition of the NMDA-evoked $^3$H-acetylcholine ($^3$H-ACh) release from corpus striatum tissue of rat brain, according to J. Lehmann and B. Scatton, Brain Research 252, 77-89 (1982) and Nature 297, 422-424 (1982).

Antagonists of NMDA-type excitatory amino acid receptors competitively antagonize NMDA-evoked $^3$H-acetylcholine ($^3$H-ACh) release from corpus striatum tissue of the brain.

The inhibition of the NMDA-evoked $^3$H-acetylcholine ($^3$H-Ach) release from rat striatal tissue slices by a compound of the invention is expressed as % of release of $^3$H-ACh in response to stimulation with 50 uM NMDA compared to control. IC$_{50}$ values represent the concentration of test compound required to inhibit the NMDA-increased $^3$H-ACh release by 50%.

The inhibitory effect on the NMDA-type excitatory amino acid receptors is demonstrated in vivo by inhibition of NMDA-induced convulsions in the mouse.

Further indicative of the anticonvulsant activity, compounds of the invention are effective in preventing audiogenic-induced seizures in DBA/2 mice (Chapman et al., Arzneim.-Forsch. 34: 1261, 1984).

The effect is determined as follows:

Forty-five minutes following compound or vehicle administration, mice are placed individually in a soundproof chamber. After a 30 second accommodation period, the mice are exposed to a sound stimulation of 110 dB for 1 minute or until the appearance of a tonic-clonic seizure. Control seizures consist of an initial wild running phase. The prevention of wild running is indicative of an anticonvulsant effect. Test compounds in either distilled water solution or in a 3% (w/v) colloidal cornstarch suspension containing 5% (w/v) polyethyleneglycol 400 and 0.34% (w/v) Tween 80, are administered by oral intubation or intraperitoneally in a volume of 10 ml/kg of body weight.

Indicative of anxiolytic activity, compounds of the invention are effective in the Cook/Davidson conflict model (Psychopharmacologia 15, 159-168 (1969)).

The aforementioned advantageous properties render the compounds of the invention useful as antagonists of the N-methyl-D-aspartate excitatory amino acid receptor in mammals and for the treatment of conditions responsive thereto, such as anxiety, convulsive disorders (epilepsy) and cerebral ischaemia.

The compounds of the invention, i.e. the compounds cited hereinabove, are prepared by (a) reducing the pyrrolyl, pyridinyl, quinolinyl or indolyl ring in a compound of the formula

(VIII)

or a functional phosphonic acid derivative thereof as defined above, wherein A has meaning as defined herein; and wherein the ring in $Y_a$ represents an unsaturated form of the ring in Y, namely 2-carboxypyrrolyl, 2-carboxypyridinyl, 2-carboxyquinolinyl or 2-carboxyindolyl all optionally substituted as defined herein by Y, and wherein the carboxy group may be functionalized in form of an ester or amide as defined herein; or reducing a double bond in a compound of the formula

(IX)

wherein Y has meaning as defined above, or a functional phosphonic acid derivative thereof, A' represents A as defined herein except for the presence of a carbon to carbon or carbon to nitrogen double bond; or (b) condensing a reactive esterified derivative of a compound of the formula

 (X)

wherein Y and A have meaning as defined herein with a diester of phosphorous acid of the formula IX, or with a phosphorus trihalide or a phosphorus tri-(lower)alkoxide of formula

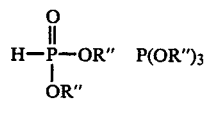

(XI)    (XII)

wherein R" advantageously represents lower alkyl and, if required, converting the resulting phosphonic acid derivative to the phosphonic acid or other ester derivative thereof;

(c) condensing, preferably under basic conditions, a compound of the formula XIII

 (XIII)

in protected form, as required, wherein Y and B have meaning as defined herein; X' represents oxygen, sulfur or N-Ra in which Ra has meaning as defined herein; with a reactive esterified derivative of a compound of the formula XIV

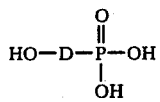

$$\text{HO—D—P(=O)(OH)—OH} \quad \text{(XIV)}$$

wherein the phosphonic acid moiety is preferably functionalized as a diester, e.g. a di-lower alkyl ester; and D has meaning as defined herein; or (d) condensing, preferably under basic conditions, a compound of the formula

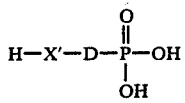

$$\text{H—X'—D—P(=O)(OH)—OH} \quad \text{(XV)}$$

wherein the phosphonic acid moiety is preferably functionalized as a diester; D has meaning as defined above; X' represents oxygen, sulfur or N-Ra in which Ra has meaning as defined herein; with a reactive esterified derivative of a compound of the formula

Y-B-OH (XVI)

wherein Y and B have meaning as defined herein;

(e) converting to $COR_1$ a substituent other than $COR_1$ at position 2 of the piperidinyl, tetrahydro-pyridinyl, perhydroindolyl, 1,2,3,4-tetrahydroquinolinyl, perhydroquinolinyl, 2,3-dihydroindolyl, dihydropyrrolyl or pyrrolidinyl ring in a compound otherwise identical to a compound of the invention; and carrying out all the said processes while, if necessary, temporarily protecting any interfering reactive group(s) in these processes, and then liberating the resulting compound of the invention; and, if desired, converting a resulting compound of the invention into another compound of the invention, and/or, if desired, converting a resulting free compound into a salt or a resulting salt into the free compound or into another salt; and/or separating a mixture of isomers or racemates obtained into the single isomers or racemates; and/or, if desired, resolving a racemate obtained into the optical antipodes.

A reactive esterified derivative of a compound, in any of the herein mentioned processes, having a hydroxy group, e.g. of a compound of formula VIII, X, XIV, XVI, represents a compound wherein hydroxy is esterified by a strong acid, especially hydrochloric, hydrobromic or hydriodic acid, or by a strong organic acid, especially a strong organic sulfonic acid, such as an aliphatic or aromatic sulfonic acid, for example methanesulfonic acid, 4-methylphenylsulfonic acid or 4-bromophenylsulfonic acid. Said reactive esterified hydroxy group is especially halo, for example chloro, bromo or iodo, or aliphatically or aromatically substituted sulfonyloxy, for example methanesulfonyloxy, phenylsulfonyloxy or 4-methylphenylsulfonyloxy (tosyloxy).

In starting compounds and intermediates which are converted to the compounds of the invention in a manner described herein, functional groups present, such as carboxy, amino (including ring NH) and hydroxy groups, are optionally protected by conventional protecting groups that are common in preparative organic chemistry. Protected carboxy, amino and hydroxy groups are those that can be converted under mild conditions into free carboxy, amino and hydroxy groups without the molecular framework being destroyed or other undesired side reactions taking place.

The purpose of introducing protecting groups is to protect the functional groups from undesired reactions with reaction components and under the conditions used for carrying out a desired chemical transformation. The need and choice of protecting groups for a particular reaction is known to those skilled in the art and depends on the nature of the functional group to be protected (carboxy group, amino group, etc.), the structure and stability of the molecule of which the substituent is a part, and the reaction conditions.

Well-known protecting groups that meet these conditions and their introduction and removal are described, for example, in J. F. W. McOmie, "Protective Groups in Organic Chemistry", Plenum Press, London, N.Y. 1973, T. W. Greene, "Protective Groups in Organic Synthesis", Wiley, New York 1981, and also in "The Peptides", Vol. I, Schroeder and Luebke, Academic Press, London, N.Y. 1965, as well as in Houben-Weyl, "Methoden der Organischen Chemie", Vol. 15/1, George Thieme Verlag, Stuttgart, 1974.

The preparation of the compounds of the invention according to process (a) relating to reduction of a compound of formula VIII is carried out by methods known in the art for the reduction of pyrrole, pyridine, indole and quinoline rings. For example, the reduction of the pyridine or quinoline ring is advantageously carried out by catalytic hydrogenation e.g. in the presence of Adams catalyst and an acidic solvent such as acetic acid to give the corresponding tetrahydropyridines, piperidines, 1,2,3,4-tetrahydroquinolines or perhydroquinolines of the invention, i.e. of formula II, IV and perhydro derivatives thereof. Quaternary quinolinium and pyridinium compounds, e.g. in which $R_2$ is lower alkyl or aryl-lower alkyl, may be similarly reduced.

The starting compounds of formula VIII for said process (a) can be prepared according to processes (b), (c) or (d) given above for the preparation of the compounds of formula I, except that in the intermediates for said processes the ring in Y, e.g. piperidyl or tetrahydroquinolinyl, is replaced by the aromatic form corresponding thereto, namely pyridine or quinoline, respectively.

The starting compounds of formula VIII for process (a) can also be prepared e.g. by first condensing a compound of the formula $R_3$-(3-, 4- or 5-pyridinyl)-A-OH or $R_4$-(3-or 4-quinolinyl)-A-OH (A, $R_3$ and $R_4$ having meaning as defined above) in form of a reactive esterified derivative, e.g. a halide such as a chloride or bromide, with a diester of formula XI in the presence of a strong base, e.g. as described in Chemical Abstracts 61, 10703, or with a tri-(lower)alkyl phosphite of formula XII to give the corresponding compounds of the formula

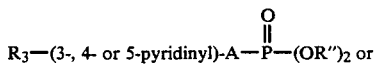

$$R_3\text{—(3-, 4- or 5-pyridinyl)-A—P(=O)—(OR'')}_2 \text{ or}$$

$$R_4\text{—(3- or 4-quinolinyl)-A—P(=O)—(O—R'')}_2$$

in which A, R'', $R_3$ and $R_4$ are as defined hereinabove.

Subsequent treatment with e.g. a peracid, such as m-chloroperbenzoic acid gives the corresponding pyridine-N-oxides or quinoline-N-oxides. Condensation with a reactive cyanide, e.g. a trialkylsilyl cyanide such as trimethylsilyl cyanide, preferably under basic conditions, e.g. in the presence of triethylamine, gives the corresponding 2-cyanopyridine or 2-cyanoquinoliine derivatives. The cyano group in the 2-cyanopyridine and 2-cyanoquinoline derivatives are then converted, by methods known in the art, to e.g. the 2-COR$_1$ (namely 2-carboxy, esterified carboxy or optionally substituted carbamoyl)-pyridine and quinoline derivatives of formula VIII as defined hereinabove.

The starting materials of formula VIII wherein X within A represents CO-NR$_b$ can be prepared by condensing a carboxylic acid of the formula Ya-B-COOH or a reactive functional derivative thereof with a compound of the formula

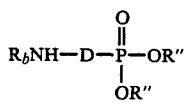

(XVII)

the symbols Ya, B, R$_b$, D, R" having meaning as defined hereinabove.

The starting materials of formula VIII wherein X within A represents R$_b$N-CO can be prepared by condensing a compound of the formula

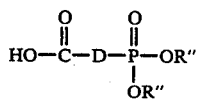

(XVIII)

or a reactive functional derivative thereof with a compound of the formula Ya-B-NHR$_b$, the symbols Ya, B, R$_b$, D, R" having meaning as defined hereinabove.

The said condensations for the preparation of said compounds of formula VIII wherein X within A represents either CO-NR$_b$ or R$_b$N-CO are carried out under conditions well-known in the art for the formation of an amide (peptide) bond, e.g. by condensation of the free acid in the presence of a condensing agent such as dicyclohexylcarbodiimide or by condensation of a reactive intermediate of the carboxylic acid, e.g. an acyl halide such as the acid chloride, or a mixed anhydride, e.g. such derived from a lower alkyl halocarbonate such as ethyl chloroformate, in an inert solvent such as methylene chloride, preferably in the presence of a basic catalyst such as pyridine.

The preparation of the compounds of formula I and derivatives according to process (a) relating to the reduction of the double bond in a compound of formula IX, is carried out by e.g. catalytic hydrogenation.

The condensation according to process (b) of a reactive esterified derivative of a compound of formula X with a compound of formula XII, e.g. triethyl phosphite, is carried out, e.g. by heating in an inert solvent, and under conditions known in the art for a Michaelis-Arbuzov reaction according to Angew. Chem. Int. Ed. 16, 477 (1977) and Chem. Rev. 81, 415 (1981). Similarly, condensation with phosphorus trichloride and subsequent hydrolysis gives a compound of formula I.

The condensation according to process (b) of a reactive ester derivative of a compound of formula X with a compound of formula XI, e.g. diethylphosphonate (diethyl phosphite), is carried out e.g. in a strong basic medium, for instance in the presence of an alkali metal such as sodium, an alkali metal hydride such as sodium hydride, an alkali metal alkoxide such as potassium t-butoxide, in an inert solvent such as toluene or dimethylformamide.

The starting materials of formula X are prepared by methods known in the art, e.g. by reduction of the corresponding pyridinyl and quinolinyl compounds.

The preparation of the compounds of the invention by processes (c) and (d) is carried out according to procedures generally known in the art for displacement of e.g. a halo, lower alkyl- or arylsulfonyloxy group by a mercaptan, an alcohol or an amine.

The preparation is carried out in a conventional manner, usually in the presence of a solvent or mixture of solvents, and, if necessary, whilst cooling or heating, for example at a temperature range of from approximately −20° C. to approximately 150° C., and/or in an inert gas atmosphere, for example a nitrogen atmosphere. The reaction is carried out advantageously in the presence of a base, such as an inorganic base, for example an alkali metal or alkaline earth metal carbonate, hydride or hydroxide, or in the presence of an organic base, such as an alkali metal lower alkoxide, or a tertiary amine such as triethylamine or pyridine.

The starting materials of formula XIII and XVI are either known in the art or are prepared by methods known in the art, e.g. by reduction of the corresponding compounds wherein the heterocyclic ring in Y is replaced by the further unsaturated or aromatic form corresponding thereto, e.g. by pyridyl in the case where the heterocycle in Y is piperidyl.

The starting materials of formula XIV and XV, and derivatives thereof, are known in the art or are prepared by methods well-known in the art.

Interconversions according to process (e) are carried out by methods well-known in the art.

Groups convertible into a COR$_1$ group are, for example, carboxy groups in form of anhydrides or acid halides, cyano, amidino groups, including cyclic amidino groups such as 5-tetrazolyl, iminoether groups, including cyclic iminoether groups, e.g., dihydro-2-oxazolinyl or dihydro-2-oxazolinyl groups substituted by lower alkyl, and also hydroxymethyl, etherified hydroxymethyl, lower alkanoyloxymethyl, trialkoxymethyl, acetyl, trihaloacetyl, halomethyl, carboxycarbonyl (COCOOH), formyl (CHO), di(lower)alkoxymethyl, alkylenedioxymethyl or vinyl.

Certain terms used in the processes have the meanings as defined below.

Trialkoxymethyl represents preferably tri(lower alkoxy)-methyl, particularly triethoxy- or trimethoxymethyl.

Etherified hydroxymethyl represents preferably lower alkoxymethyl, lower alkoxyalkoxymethyl such as methoxymethyloxymethyl, 2-oxa- or 2-thiacyclo-alkoxymethyl, particularly 2-tetrahydropyranyloxymethyl.

Halomethyl represents especially chloromethyl but may also be bromomethyl or iodomethyl.

An alkali metal represents preferably lithium but may also be potassium or sodium.

Groups convertible into COR$_1$=carboxy include esters and amides, and such are not limited to ester and amide derivatives as defined herein for COR$_1$. Conversion to carboxy is generally accomplished by solvolysis, with acid or base.

Benzyl esters or nitrobenzyl esters may be converted into the carboxy group by catalytic hydrogenation, the latter also with chemical reducing agents, e.g., sodium dithionite or with zinc and a carboxylic acid. In addition, tert-butyl esters may also be cleaved with trifluoroacetic acid.

Acetyl may be oxidatively cleaved to carboxy by conversion first to trihaloacetyl, e.g. tribromo-or triiodoacetyl, by treatment e.g. with sodium hypobromite, followed by cleavage with e.g. an aqueous base, such as sodium hydroxide.

Formyl, di(lower)-alkoxymethyl or alkylenedioxymethyl (formyl protected in the form of an acetal), e.g. the dimethyl acetal, are oxidized with e.g. silver nitrate, pyridinium dichromate or ozone to carboxy.

Vinyl may be converted to carboxy by ozonolysis to formyl, which is in turn oxidized to carboxy.

Hydrolysis of trialkoxymethyl to carboxy is advantageously carried out with inorganic acids such as hydrohalic or sulfuric acid. Hydrolysis of etherified hydroxymethyl to hydroxymethyl is preferably carried out with solutions of inorganic acids such as a hydrohalic acid. Hydroxymethyl is in turn oxidized to carboxy with an oxidizing agent such as pyridinium dichromate.

Halomethyl may also be converted to the corresponding carboxaldehydes with e.g. dimethylsulfoxide in the presence of triethylamine and silver tetrafluoroborate, or with chromium trioxide and pyridine in methylene chloride.

The conversion of cyano to lower alkoxycarbonyl is advantageously carried out by treatment first with a lower alkanol, e.g. anhydrous ethanol, in the presence of a strong acid, e.g. hydrochloric acid preferably at reflux temperature, followed by hydrolysis with water.

Furthermore, the conversion of cyano to carbamoyl is preferably carried out by treatment with an alkali metal hydroxide, e.g. dilute sodium hydroxide, and hydrogen peroxide, preferably at room temperature.

Esterified carboxy such as lower alkoxycarbonyl may be amidized with ammonia, mono- or di-(lower)alkylamines e.g. methylamine, dimethylamine in an inert solvent, e.g. a lower alkanol, such as butanol, to unsubstituted, mono- or di(lower)alkylcarbamoyl.

The compounds of the invention may thus also be converted to other compounds of the invention by e.g. functional group transformations well-known in the art.

For example, conversion of carboxylic acid esters and amides to carboxylic acids is advantageously carried out by hydrolysis with inorganic acids such as a hydrohalic or sulfuric acid or with aqueous alkalies, preferably alkali metal hydroxides such as lithium or sodium hydroxide.

Free carboxylic acids may be esterified with lower alkanols, such as ethanol, in the presence of a strong acid, e.g. sulfuric acid, or with diazo-lower alkanes, e.g. diazomethane in a solvent such as ethyl ether, advantageously at room temperature, to give the corresponding lower alkyl esters.

Furthermore, the free carboxylic acids may be converted via treatment of a reactive intermediate thereof, e.g. an acyl halide such as the acid chloride, or a mixed anhydride, e.g. such derived from a lower alkyl halocarbonate such as ethyl chloroformate, with ammonia, mono- or di-(lower)alkylamines, in an inert solvent such as methylene chloride, preferably in the presence of a basic catalyst such as pyridine, to compounds wherein $COR_1$ represents unsubstituted, mono or di-(lower)-alkylcarbamoyl.

Phosphonic acid esters are converted to the corresponding phosphonic acids by treatment with acid, such as aqueous hydrochloric acid or hydrobromic acid in glacial acetic acid, or with iodotrimethylsilane or bromotrimethylsilane according to J. Chem. Soc. Chem. Comm. 1979, 739. Benzyl esters may be converted to the acids by hydrogenolysis.

Phosphonic acids are converted to esters, e.g. optionally substituted lower alkyl esters, e.g. by condensation with an optionally substituted lower alkyl halide preferably in a basic non-aqueous medium, such as in the presence of triethylamine.

The compounds of the invention wherein X represents S can be oxidized to the corresponding compounds wherein X represents SO with an appropriate oxidizing agent such as sodium periodate, or to the corresponding compounds wherein X represents $SO_2$ with a stronger oxidizing agent, such as m-chloroperbenzoic acid.

Compounds of the invention and intermediates wherein X represents $NR_b$-CO or CO-$NR_b$ can be reduced to the amines of identical chain length (wherein X represents $NR_a$) by treatment with a reducing agent known in the art for the selective reduction of the amide grouping to the corresponding amine.

The compounds of the invention and intermediates wherein Y represents optionally substituted 2-carboxytetrahydropyridinyl, tetrahydroquinolinyl or dihydropyrrolyl and derivatives thereof are converted to the corresponding piperidinyl, perhydroquinolinyl, or pyrrolidinyl compounds, respectively, e.g. by catalytic hydrogenation.

The above-mentioned reactions are carried out according to standard methods, in the presence or absence of diluents, preferably such as are inert to the reagents and are solvents thereof, of catalysts, condensing or said other agents respectively and/or inert atmospheres, at low temperatures, room temperature or elevated temperatures preferably at the boiling point of the solvents used, and at atmospheric or super-atmospheric pressure. The preferred solvents, catalysts and reaction conditions are set forth in the appended illustrative examples.

The invention further includes any variant of the present processes, in which an intermediate product obtainable at any stage thereof is used as starting material and the remaining steps are carried out, or the process is discontinued at any stage thereof, or in which the starting materials are formed under the reaction conditions, or in which the reaction components are used in the form of their salts or optically pure antipodes.

Mainly those starting materials should be used in said reactions, that lead to the formation of those compounds indicated above as being especially preferred.

The invention also relates to any novel starting materials and processes for their manufacture.

Depending on the choice of starting materials and methods, the new compounds may be in the form of one of the possible isomers or mixtures thereof, for example, depending on the number of asymmetrical carbon atoms, as pure optical isomers, such as antipodes, as mixtures of optical isomers such as racemates or as mixtures of diastereoisomers or of geometric isomers. The aforesaid possible isomers or mixtures thereof are within the purview of this invention; certain particular isomers are preferred as indicated above.

Any resulting mixtures of diastereoisomers, mixtures of racemates can be separated on the basis of the physicochemical differences of the constituents, in known manner, into the pure isomers, diastereoisomers racemates, or geometric isomers, for example by chromatography and/or fractional crystallization.

Any resulting racemates can be resolved into the optical antipodes by known methods, for example by e.g. reacting an acidic end product with an optically active base that forms salts with the racemic acid, and separating the salts obtained in this manner, for example by fractional crystallization, into the diastereoisomeric salts from which the optically active free carboxylic or phosphonic acid antipodes can be liberated on acidification. The basic racemic products can likewise be resolved into the optical antipodes, e.g. by separation of the diastereoisomeric salts thereof, with an optically active acid, and liberating the optically active basic compound by treatment with a standard base. Racemic products of the invention can thus be resolved into their optical antipodes, e.g., by the fractional crystallization of d- or l-(tartrates, mandelates, camphorsulfonates) or of d- or l-($\alpha$-methylbenzylamine, cinchonidine, cinchonine, quinine, quinidine, ephedrine, dehydroabietylamine, brucine or strychnine) salts. Advantageously, the more active of the two antipodes is isolated.

Finally the compounds of the invention are either obtained in the free form, or as a salt thereof. Any resulting base can be converted into a corresponding acid addition salt, preferably with the use of a therapeutically useful acid or anion exchange preparation, or resulting salts can be converted into the corresponding free bases, for example, with the use of a stronger base, such as a metal or ammonium hydroxide or a basic salt, e.g. an alkali metal hydroxide or carbonate, or a cation exchange preparation, or an alkylene oxide such as propylene oxide. A compound of the invention with a free carboxylic or phosphonic acid group can thus also be converted into the corresponding metal or ammonium salts. These or other salts, for example, the picrates, can also be used for purification of the bases obtained; the bases are converted into salts, the salts are separated and the bases are liberated from the salts.

In view of the close relationship between the free compounds and the compounds in the form of their salts, whenever a compound is referred to in this context, a corresponding salt is also intended, provided such is possible or appropriate under the circumstances.

The compounds, including their salts, can also be obtained in the form of their hydrates, or include other solvents used for their crystallization.

The pharmaceutical compositions according to the invention are those suitable for enteral, such as oral or rectal, transdermal and parenteral administration to mammals, including man, for blockade of the N-methyl-D-aspartate excitatory amino acid receptor and for the treatment of diseases responsive to blockade of the N-methyl-D-aspartate excitatory amino acid receptor, such as cerebral ischaemia, convulsive disorders and anxiety, comprising an effective amount of a pharmacologically active compound of the invention, alone or in combination with one or more pharmaceutically acceptable carriers.

The pharmacologically active compounds of the invention are useful in the manufacture of pharmaceutical compositions comprising an effective amount thereof in conjunction or admixture with excipients or carriers suitable for either enteral or parenteral application. Preferred are tablets and gelatin capsules comprising the active ingredient together with (a) diluents, e.g. lactose, dextrose, sucrose, mannitol, sorbitol, cellulose and/or glycine; (b) lubricants, e.g. silica, talcum, stearic acid, its magnesium or calcium salt and/or polyethyleneglycol; for tablets also (c) binders e.g. magnesium aluminum silicate, starch paste, gelatin, tragacanth, methylcellulose, sodium carboxymethylcellulose and/or polyvinylpyrrolidone; if desired (d) disintegrants, e.g. starches, agar, alginic acid or its sodium salt, or effervescent mixtures; and/or (e) absorbents, colorants, flavors and sweeteners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1 to 75%, preferably about 1 to 50%, of the active ingredient.

Suitable formulations for transdermal application include an effective amount of a compound of formula I with carrier. Advantageous carriers include absorbable pharmacologically acceptable solvents to assist passage through the skin of the host. Characteristically, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

The invention also relates to a method of blocking the N-methyl-D-aspartate excitatory amino acid receptor in mammals, and to a method of treatment of disorders in mammals, e.g. such responsive to blockade of the N-methyl-D-aspartate excitatory amino acid receptor, such as cerebral ischaemia, convulsive disorders and anxiety, using an effective amount of a compound of the invention as a pharmacologically active substance, preferably in the form of above-cited pharmaceutical compositions. The dosage of active compound administered is dependent on the species of warm-blooded animal (mammal), the body weight, age and individual condition, and on the form of administration.

A unit dosage for a mammal of about 50 to 70 kg may contain between about 10 and 100 mg of the active ingredient.

The following examples are intended to illustrate the invention and are not to be construed as being limitations thereon. Temperatures are given in degrees Centigrade. If not mentioned otherwise, all evaporations are performed under reduced pressure, preferably between about 15 and 100 mmHg.

EXAMPLE 1

4-[(N-acetyl-N-diethylphosphonomethyl)-aminomethyl]-pyridine-2-carboxamide (2.0 g) is hydrogenated in 50 ml of glacial acetic acid with 0.8 g of platinum oxide catalyst at 3 atmospheres pressure for 16 hours to afford after filtration and removal of solvent, cis-4-[(N-diethylphosphonomethyl-N-acetyl)-aminomethyl]-piperidine-2-carboxamide.

The starting material is prepared as follows:

A mixture of 4 g of 4-picolyl chloride, 10 g of calcium carbonate and 6 g of diethyl aminomethylphosphonate in 40 ml of dimethylformamide is stirred at 100° for 16 hours. After filtration and removal of solvent the residue is dissolved in methylene chloride and treated with 4 g of acetic anhydride. After 1 hour the solvent is removed and the residue is chromatagraphed on silica gel to afford 4-[(N-acetyl-N-diethylphosphonomethyl)-aminomethyl]-pyridine as an oil. A solution of 3.0 g of the crude compound in 30 ml of methylene chloride is treated with 1.8 g of m-chloroperbenzoic acid. After 10 hours at room temperature the solvent is removed in vacuo and the residue is heated at 100° for 2 hours with 5 ml of trimethylsilyl cyanide and 10 ml of triethylamine. After removal of solvent the residue is dissolved in methylene chlorde and washed with saturated sodium bicarbonate. Drying and removing the solvent affords 2-cyano-4-[(N-acetyl-N-di-ethylphosphonomethyl)-aminomethyl]-pyridine as an oil. This material is heated at 70° for 10 minutes in 10 ml of concentrated sulfuric acid. After dilution with methylene chloride and washing with saturated sodium carbonate the solution is dried and the solvent removed to afford 4-[(N-acetyl-N-diethylphosphonomethyl)-aminomethyl]-pyridine-2-carboxamide.

EXAMPLE 2

A solution of 1 g of cis-4-[N-diethylphosphonomethyl-N-acetyl)-aminomethyl]-piperidine-2-carboxamide in 3.0 ml of 6N hydrochloric acid is heated under reflux for 18 hours. After removal of the solvent the residue is dissolved in 80% ethanol and treated with excess propylene oxide. After evaporation of the solvent the residue is dissolved in water and filtered through Dowex 50 W-X8 strongly acidic cation ion exchange resin to afford after evaporation to dryness cis-4-[(N-phosphonomethyl)-aminomethyl]-piperidine-2-carboxylic acid.

EXAMPLE 3

A solution of 3.0 g of N-benzyl-4-[(N-acetyl-N-2-diethylphosphonoethyl-amino]-pyridine-2-carboxamide in 50 ml of glacial acetic acid is hydrogenated over 1.0 g of platinum oxide at 3 atmospheres pressure for 16 hours. Filtration and removal of solvent in vacuo affords N-benzyl-cis-4-[(N-acetyl-N-(2-diethylphosphonoethyl)-amino]-piperidine-2-carboxamide.

The starting material is prepared as follows:

A mixture of 5 g of methyl 4-chloropicolinate and 3.44 g of benzylamine is heated at 100° for 16 hours. Cooling and trituration with ether/hexane affords N-benzyl-4-chloro-pyridine-2-carboxamide. This material is heated with 5 g of sodium azide in 50 ml of dimethylformamide at 100° for 10 hours. After dilution with water the product is extracted with ether. Drying and removing the solvent affords 4-azido-N-benzyl-pyridine-2-carboxamide as an oil. This material is stirred under 1 atom of hydrogen in 50 ml of ethanol with 1.0 g of 10% palladium on carbon catalyst for 4 hours. Filtration and removal of solvent affords 4-aminopyridine-2-(N-benzyl)-carboxamide as an oil.

A mixture of 2 g of 4-aminopyridine-2-(N-benzyl)-carboxamide, 10 g of calcium carbonate and 5 g of diethyl 2-bromoethylphosphonate in 20 ml of dimethylformamide is heated at 100° for 16 hours. After filtration and removal of solvent, the residue is dissolved in methylene chloride and treated with 1.5 g of acetic anhydride. After 1 hour at room temperature the solvent is removed and the residue chromatographed on silica gel to afford 4-[(N-acetyl-N-(2-diethylphosphonoethyl)-amino]-pyridine-2-(N-benzyl)-carboxamide.

EXAMPLE 4

A solution of 1 g of cis-4-[(N-acetyl-N-(2-diethylphosphonoethyl)-amino]-piperidine-2-(N-benzyl)-carboxamide in 30 ml of 6N hydrochloric acid is refluxed for 18 hours. After removal of solvent in vacuo the residue is dissolved in 80% ethanol and treated with excess propylene oxide. After removal of solvent the residue is dissolved in water and filtered through Dowex 50W-X8 resin to afford after removal of solvent cis-4-(2-phosphonoethylamino)-piperidine-2-carboxylic acid.

EXAMPLE 5

A mixture of 1.0 g of methyl 4-($\alpha$-dimethylphosphonoacetamido)-picolinate, 500 mg of platinum oxide in 20 ml of acetic acid is hydrogenated at 4 atmospheres pressure for 60 hours. After filtration and removal of solvent, the residue is dissolved in methylene chloride and stirred with 5 g of anhydrous $Na_2CO_3$. After filtration and standing for 16 hours the solvent is removed to afford cis-2-methoxycarbonyl-4-($\alpha$-diethylphosphonoacetamido)-piperidine as a viscous oil.

The starting material is prepared as follows:

A mixture of 2.0 g of methyl 4-chloropicolinate and 2 g of sodium azide in 20 ml of dimethylformamide is stirred at 100° for 8 hours. The solvent is removed in vacuo, the reaction is diluted with water and the product extracted into ethyl acetate. After drying over magnesium sulfate, the solvent is removed in vacuo. The residue is hydrogenated in 30 ml of ethanol at atmospheric pressure over 500 mg of 10% palladium on carbon catalyst for 3 hours. After filtration through filter-cel the solvent is removed in vacuo and the residue crystallized from ether to afford methyl 4-aminopicolinate.

A mixture of 1.0 g of methyl 4-aminopicolinate, 1.0 g of $\alpha$-(dimethylphosphono)-acetic acid and 1.0 g of dicyclohexylcarbodiimide in 10 ml of methylene chloride is stirred at room temperature for 6 hours. After filtration and removal of solvent the residue is chromatographed on silica gel with 5% methanol/methylene chloride as the eluent to afford methyl 4-($\alpha$-dimethylphosphonoacetamido)-picolinate as a viscous oil.

EXAMPLE 6

A mixture of 900 mg of cis-2-methoxycarbonyl-4-($\alpha$-dimethylphosphonoacetamido)-piperidine and 20 ml of methylene chloride is treated with 4 g trimethylsilyl iodide and the resulting mixture is stirred for 16 hours at room temperature. After removal of solvent the residue is stirred with water for 15 minutes and the solvent is removed in vacuo. A solution of the residue in 30 ml of 3N hydrochloric acid is heated under reflux for one hour and evaporated to dryness. A solution of the residue in 15 ml ethanol is treated with 1 ml of propylene oxide. Evaporation to dryness yields cis-4-($\alpha$-phosphonoacetamido)-piperidine-2-carboxylic acid.

EXAMPLE 7

A solution of 200 mg of 4-($\alpha$-phosphonoacetamido)-picolinic acid in 50 ml of water is hydrogenated over 1.0 g of platinum oxide at 3 atmospheres pressure for 8 hours. After filtration and evaporation to dryness the residue is triturated with ethanol to afford 4-($\alpha$-phosphonoacetamido)-piperidine-2-carboxylic acid as a mixture of cis and trans isomers.

The starting material is prepared as follows:

A solution of 1.0 g of methyl 4-(α-dimethylphosphonoacetamido)-picolinate and 2.2 ml of trimethylsilyl iodide in 10 ml of methylene chloride is allowed to stand at 25° for four hours. The reaction mixture is evaporated to dryness, the residue is dissolved in 20 ml of ethanol, and 2 ml of propylene oxide is added to precipitate methyl 4-(α-phosphonoacetamido)-picolinate; m.p. 190°–195° dec.

A mixture of 377 mg of methyl 4-(α-phosphonoacetamido)-picolinate and 4.2 ml of 1N sodium hydroxide is heated at 80° for 10 minutes. The reaction mixture is cooled, filtered through Dowex 50-X8 resin and evaporated to dryness. Trituration with ethanol affords 4-(α-phosphonoacetamido)-picolinic acid, m.p. 249°–252° (dec).

EXAMPLE 8

The following compounds may be prepared from appropriate starting materials using procedures similar to those described in the previous examples:
(a) cis-4-(α-phosphonoacetamido)-1,2,3,4-tetrahydroquinoline-2-carboxylic acid;
(b) cis-4-(phosphonomethoxymethyl)-piperidine-2-carboxylic acid;
(c) cis-4-(2-phosphonoethoxy)-piperidine-2-carboxylic acid;
(d) cis-4-(2-phosphonoethylamino-1,2,3,4-tetrahydroquinoline-2-carboxylic acid.

EXAMPLE 9

Preparation of an injectable formulation containing 10 mg of the active ingredient per 5 ml of solution:
Formula

| | |
|---|---|
| cis-4-(2-phosphonoethylamino)-piperidine-2-carboxylic acid | 10.0 g |
| Propylparaben | 0.5 g |
| Water for injection q.s. | 5000.0 ml |

The active ingredient and preservative are dissolved in 3500 ml of water for injection and the solution is diluted to 5000 ml. The solution is filtered through a sterile filter and filled into injection vials under sterile conditions, each vial containing 5 ml of the solution.

What is claimed is:

1. A compound of the formula

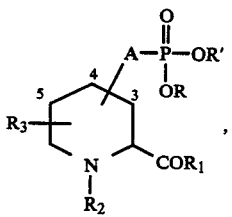

(II)

or a compound of formula II with a double bond present between the 3 and 4 or between the 4 and 5 carbon atoms of the piperidyl ring, so as to form a tetrahydropyridinyl ring in which the phosphono bearing chain is attached at the 3, 4, or 5-position of the piperidinyl or tetrahydropyridinyl ring, and wherein R and R' represent hydrogen, lower alkyl, benzyl, benzyl substituted on phenyl by halogen, lower alkyl or lower alkoxy, lower alkanoyloxymethyl, lower alkanoyloxymethyl substituted on oxymethyl by lower alkyl, cyclohexyl or cyclopentyl; $R_2$ represents hydrogen, lower alkyl, aryl-lower alkyl or lower alkanoyl; $R_3$ represents hydrogen, lower alkyl or aryl-lower alkyl; $COR_1$ represents carboxy or carboxy derivatized in the form of a pharmaceutically acceptable ester; A represents $$(CH_2)_m\text{-}X\text{-}(CH_2)_n \qquad (A)$$

$(CH_2)_m$ being attached to the ring, wherein m represents zero, 1, 2 or 3; n represents 1, 2 or 3; X represents O, S, SO, $SO_2$, $CO\text{-}NR_b$, $R_bN\text{-}CO$ or $N\text{-}R_a$; $R_a$ represents hydrogen, lower alkyl, aryl, aryl-lower alkyl or acyl; $R_b$ represents hydrogen, lower alkyl or aryl-lower alkyl; and wherein one or more of carbon atoms within A may be substituted by lower alkyl; acyl in the above definitions represents lower alkanoyl, lower alkoxycarbonyl, aryl-lower alkanoyl or aryl-lower alkoxycarbonyl; aryl in the above definitions represents phenyl or phenyl substituted by lower alkyl, lower alkoxy or halogen; and carboxy esterified in form of a pharmaceutically acceptable ester represents lower alkoxycarbonyl, (amino, mono- or di-lower alkylamino)-substituted straight chain $C_2$–$C_5$-lower alkoxycarbonyl, carboxy substituted lower alkoxycarbonyl, lower alkoxycarbonyl-substituted lower alkoxycarbonyl, benzyloxycarbonyl, pyridylmethoxycarbonyl, lower alkanoyloxy-substituted methoxycarbonyl, (lower alkanoyloxy or lower alkoxy)-substituted lower alkoxymethoxycarbonyl, bicyclo[2,2,1]heptyloxycarbonyl-substituted methoxycarbonyl, 3-phthalidoxycarbonyl, (lower alkyl, lower alkoxy, halo)-substituted 3-phthalidoxycarbonyl or lower alkoxycarbonyloxy-lower alkoxycarbonyl; or a pharmaceutically acceptable salt thereof.

2. A compound according to claim 1 of formula II wherein R and R' independently represent hydrogen, benzyl, lower alkyl, lower alkanoyloxymethyl or lower alkanoyloxymethyl substituted on oxymethyl by lower alkyl, cyclohexyl or cyclopentyl; A represents $(CH_2)_m\text{-}X\text{-}(CH_2)_n$; m represents zero, 1 or 2; n represents 1 or 2; X represents O, S, SO, $SO_2$, $CO\text{-}NR_b$, $R_bN\text{-}CO$ or $NR_a$; $R_a$ represents hydrogen, lower alkyl, benzyl or lower alkanoyl; $R_b$ represents hydrogen, lower alkyl or benzyl; $COR_1$ represents carboxy or carboxy esterified in form of a pharmaceutically acceptable ester as defined in said claim; $R_2$ and $R_3$ represent hydrogen or lower alkyl; or a pharmaceutically acceptable salt thereof.

3. A compound according to claim 1 of the formula

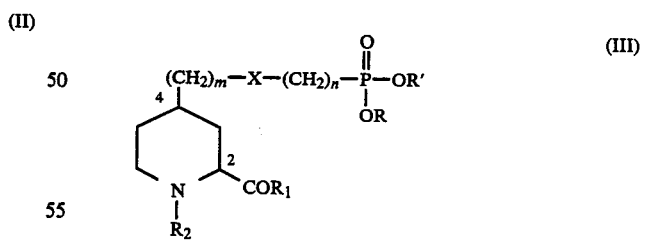

(III)

wherein m represents zero or the integer 1 or 2; n represents the integer 1 or 2; X represents O, S, $SO_2$, $CO\text{-}NR_b$, $R_bN\text{-}CO$ or $N\text{-}R_a$ in which $R_a$ represents hydrogen, lower alkyl or lower alkanoyl, and $R_b$ represents hydrogen or lower alkyl; R and R' independently represent hydrogen, lower alkyl, benzyl, lower alkanoyloxymethyl or lower alkanoyloxymethyl substituted on oxymethyl by lower alkyl; $COR_1$ represents carboxy or carboxy esterified in the form of a pharmaceutically acceptable ester as defined in said claim; $R_2$ represents hydrogen, lower alkyl or lower alkanoyl; or a pharmaceutically acceptable salt of any said compound having a salt-forming functional grouping.

4. A pharmaceutical composition suitable for the blockade of the N-methyl-D-aspartate excitatory amino acid receptor in a mammal comprising a correspondingly effective amount of a compound of claim 1 in combination with one or more pharmaceutically acceptable carriers.

5. A compound according to claim 3 of formula III wherein the 2 and 4 substituents are cis to each other.

6. A compound according to claim 3 of formula III wherein m represents zero or the integer 1 or 2; X represents O, S, CO-$NR_b$, $R_b$N-CO or N-Ra as defined in said claim; n represents the integer 1 or 2; R and R' both represent hydrogen, lower alkyl or lower alkanoyloxymethyl; or one of R and R' represents hydrogen and the other of R and R' represents lower alkyl, benzyl, lower alkanoyloxymethyl or lower alkanoyloxymethyl substituted on oxymethyl by lower alkyl; $R_2$ represents hydrogen; $COR_1$ represents carboxy or carboxy esterified in form of a pharmaceutically acceptable ester comprising a straight chain $C_1$-$C_4$-alkyl ester, a lower alkanoyloxymethyl ester, a di-lower alkylamino-straight chain $C_2$-$C_4$-alkyl ester or a pyridylmethyl ester; or a pharmaceutically acceptable salt thereof.

7. A compound according to claim 3 of formula III wherein m represents zero or 1; X represents NH-CO, N-(lower alkyl)-CO, NH or N-lower alkyl; n represents the integer 1 or 2; R and R' represent hydrogen; $COR_1$ represents carboxy or carboxy esterified in form of a pharmaceutically acceptable ester comprising a straight chain $C_1$-$C_4$-alkyl ester, a lower alkanoyloxymethyl ester, a di-lower alkylamino-straight chain $C_2$-$C_4$-alkyl ester or a pyridylmethyl ester; $R_2$ represents hydrogen; or a pharmaceutically acceptable salt thereof.

8. A compound according to claim 7 of formula III wherein the 2 and 4 substituents are cis to each other.

9. A compound according to claim 7 being 4-($\alpha$-phosphonoacetamido)-piperidine-2-carboxylic acid or a pharmaceutically acceptable salt thereof.

10. A compound according to claim 7 being 4-(2-phosphonoethylamino)piperidine-2-carboxylic acid or a pharmaceutically acceptable salt thereof.

11. A method of blocking the N-methyl-D-aspartate excitatory amino acid receptor in a mammal comprising the administration to a mammal in need thereof of a correspondingly effective amount according to a compound of claim 1.

12. A method of treating diseases responsive to N-methyl-D-aspartate excitatory amino acid receptor blockade in mammals comprising the administration to a mammal in need thereof of an effective N-methyl-D-aspartate excitatory amino acid receptor blocking amount of a compound according to claim 1 or of a pharmaceutical composition comprising said compound.

13. A method of treating cerebral ischaemia, epilepsy or anxiety in mammals comprising the administration to a mammal in need thereof of an effective N-methyl-D-aspartate excitatory amino acid receptor blocking amount according to of a compound of claim 3.

14. A pharmaceutical composition for the treatment of epilepsy in mammals comprising an effective amount of a compound of claim 1 in combination with one or more pharmaceutically acceptable carriers.

15. A pharmaceutical composition for the treatment of epilepsy in mammals comprising an effective amount of a compound of claim 3 in combination with one or more pharmaceutically acceptable carriers.

16. A method of treating epilepsy in mammals comprising the administration to a mammal in need thereof of an effective amount according to a compound of claim 1.

* * * * *